United States Patent [19]

Minkkinen

[11] 4,263,019
[45] Apr. 21, 1981

[54] VAPOR RECOVERY

[75] Inventor: Ari A. Minkkinen, Versailles, France

[73] Assignee: The Lummus Company, Bloomfield, N.J.

[21] Appl. No.: 86,456

[22] Filed: Oct. 19, 1979

[51] Int. Cl.³ .................... B01D 11/04; B01D 53/14
[52] U.S. Cl. ............................... 55/37; 55/48; 55/49; 55/89; 208/341; 585/804
[58] Field of Search ............... 55/37, 48, 49, 88, 89; 208/341; 585/804, 833

[56] References Cited

U.S. PATENT DOCUMENTS

| | | | |
|---|---|---|---|
| 1,463,782 | 8/1923 | Armstrong | 208/341 X |
| 2,180,496 | 11/1939 | Balcar | 55/48 |
| 2,395,362 | 2/1946 | Welling | 55/37 |
| 2,659,453 | 11/1953 | Robinson | 55/37 |
| 3,466,344 | 9/1969 | De Graff et al. | 585/804 X |
| 3,499,043 | 3/1970 | Kling | 585/833 X |
| 3,828,099 | 8/1974 | Sato et al. | 55/37 X |
| 4,038,332 | 7/1977 | Carter | 55/48 X |
| 4,066,423 | 1/1978 | McGill et al. | 55/48 |

*Primary Examiner*—Robert H. Spitzer
*Attorney, Agent, or Firm*—Louis E. Marn; Elliot M. Olstein

[57] ABSTRACT

Volatile liquid, such as benzene, isoprene, cyclopentadiene, butadiene present as a vapor in a blanket gas released from a storage zone for the liquid is absorbed from the gas by use of an absorption oil, followed by contacting of the rich absorption oil with an immiscible extraction solvent in an amount much less than the absorption oil to extract absorbed volatile liquid and provide a lean absorption oil. The volatile liquid is recovered from the extraction solvent, for example, by stripping. By recovering the volatile liquid from the small amount of extraction solvent, rather than the absorption oil, heating and cooling duties are decreased.

15 Claims, 1 Drawing Figure

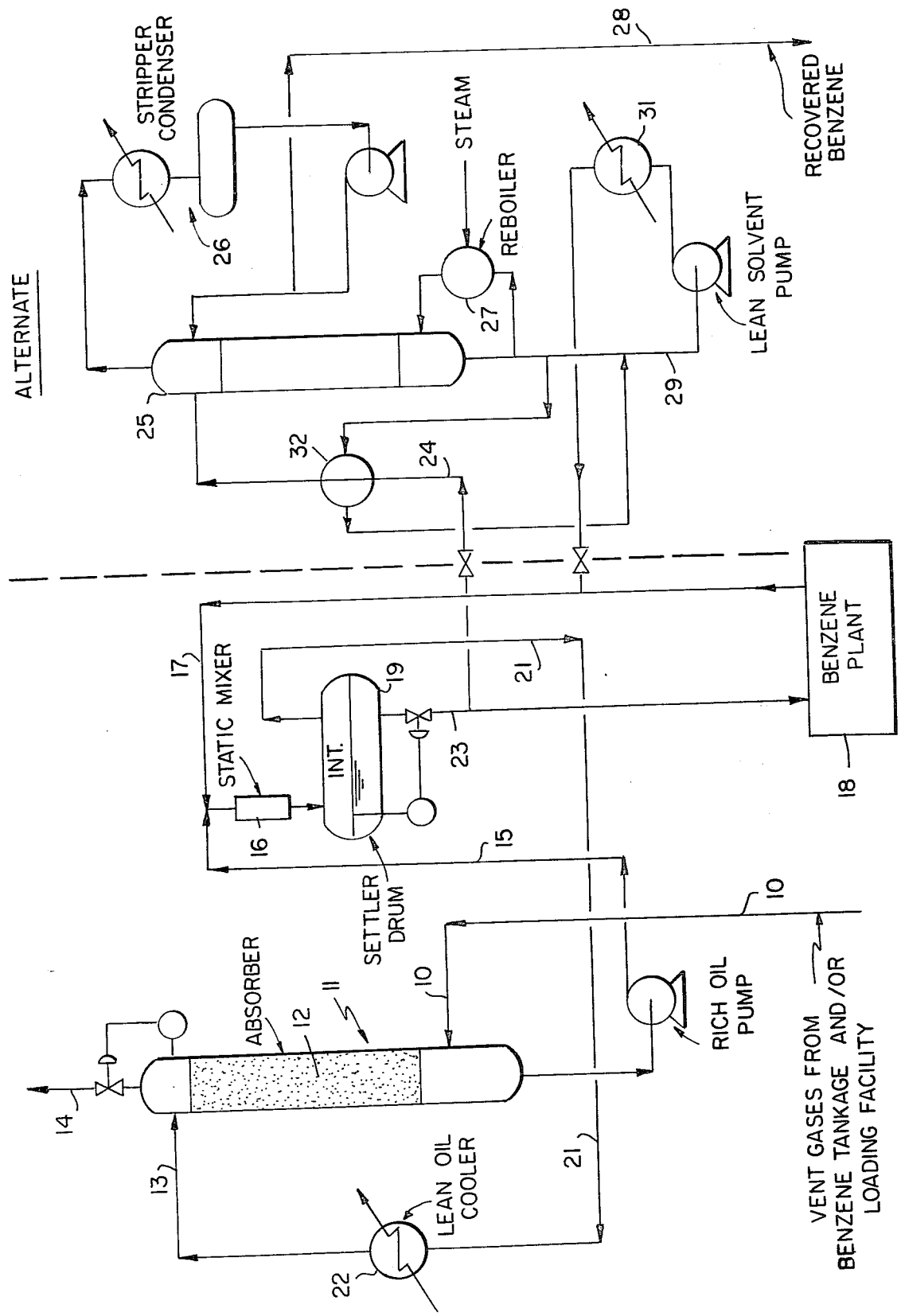

VAPOR RECOVERY

This invention relates to vapor recovery. More particularly, the present invention relates to recovery of a volatile liquid present as a vapor in a blanket gas released from a storage zone for the liquid. Still more particularly, this invention relates to the recovery of benzene vapor from a blanket gas released from a benzene storage zone.

Volatile liquids are present in storage zones, such as storage tanks, tank cars, tank trucks, ships, barges and the like, and in loading and unloading such storage zones, a blanket gas, such as nitrogen, containing the volatile liquid, in vapor form, is released from such storage zones. The vapor present in such gas represents a potential loss of valuable product. In addition, such vaporized liquid may present a pollution problem. Thus, for example, benzene is recognized as an occupational hazard, and as a result, it is necessary to limit the quantities of benzene which are released into the atmosphere.

In order to reduce benzene emission during loading and unloading operations, the following routes are presently available:
1. Return tank car or truck vapors to product tank vapor space when the product tank is of a cone roof design.
2. Burn vent gases in a localized flare.
3. Incorporate in-situ self contained vapor recovery units to condense or absorb benzene from the vent gas.

Each of the presently available systems has certain inherent disadvantages. Thus, for example, the burning of the vent gases represents a potential product loss; e.g., a typical medium to large size benzene plant could result in 300,000 to 500,000 dollars of product loss revenue per year. The conventional in-situ units for effecting vapor recovery, which utilize compression and cooling require mechanically complex equipment. Other conventional in-situ absorption units require substantial heating duties to effect recovery of the benzene from the rich absorption oil. As a result, there is a need for an improved system for effecting recovery of a volatile liquid, in vapor form, present in a blanket gas released from a storage zone for the liquid.

In accordance with the present invention, there is provided a process for separating a volatile liquid present as a vapor in a blanket gas released from a storage zone for the volatile liquid, wherein the gas containing the volatile liquid is contacted in-situ with an absorption oil to absorb the volatile liquid vapor from the gas and produce a rich absorption oil containing absorbed volatile liquid. The rich absorption oil is then contacted in-situ with an extraction solvent, which is immiscible with the absorption oil, to extract the volatile liquid from the rich absorption oil and provide a lean absorption oil for recycle to the in-situ absorption. The rich extraction solvent is separated in-situ and the volatile liquid recovered therefrom to provide a lean extraction solvent for recycle to the in-situ extraction step. Applicant has found that the ratio of extraction solvent to volatile liquid is lower than the ratio of absorption oil to gas containing volatile liquid, whereby the volatile liquid can be recovered from the extraction solvent, for example, by stripping, with lower heating and cooling requirements.

The invention will be further described with respect to a process for separating the volatile liquid benzene from a blanket gas released from a storage zone; however, the scope of the invention should not be limited by such description.

The drawing is a simplified schematic flow diagram of an embodiment of the present invention for separating benzene vapor from a blanket gas.

Referring now to the drawing, a blanket gas released from a benzene storage zone, such as a storage tank, railroad car, and the like, which contains benzene in vapor form, in line 10 is introduced into the bottom of an absorption tower, schematically generally indicated as 11, which contains suitable packing, indicated as 12 for increasing gas-liquid contact. A cooled lean absorption oil for absorbing benzene from the gas is introduced into the top of tower 11 through line 13. The absorption oil is one which is suitable for effectively removing benzene from a gas by absorption, and such an absorption oil generally has an aliphatic character. In addition, such an absorption oil should preferably have a boiling point of at least 400° F. It is to be understood that although the absorption oil must have a paraffinic character, the oil can contain some aromatics. Thus, for example, a low aromatic content kerosene, diesel or gas oil is acceptable. The selection of a suitable absorption oil for absorbing benzene from a gas is deemed to be well within the scope of those skilled in the art from the teachings herein.

In general, the absorption tower 11 is operated at a temperature in the order of from 100° F. to 130° F., and at a pressure equal to the tank loading conditions, generally, of from 2.0 to 10 psig. In addition, the tower is operated at molar liquid to gas ratios, which are generally in the order of at least 2 to 1, in order to effect essentially complete absorption of the benzene from the gas introduced through line 10.

A gas essentially free of benzene is released from tower 11 through line 14. In most cases, the gas in line 14 contains less than 1 mole per million, and most preferably less than 0.5 mole per million of benzene.

Benzene rich absorption oil is withdrawn from the bottom of tower 11 through line 15 and is introduced into an in-line static mixer 16 along with lean extraction solvent in line 17. The extraction solvent in line 17 is one which is capable of effectively extracting essentially all the benzene from the rich absorption oil, and in addition, such extraction solvent must be immiscible with the absorption oil. Thus, the extraction solvent employed in line 17 is one which has a high solvency for benzene and which is also immiscible with the absorption oil having a generally aliphatic character. As representative examples of such extraction solvents, there may be mentioned glycols, such as the di-, tri- and tetra-ethylene glycols, sulfolane, N-methyl pyrollidone, and the like. The selection of a suitable extraction solvent is deemed to be well within the scope of those skilled in the art from the teachings herein.

In accordance with one embodiment of the present invention wherein a blanket gas containing benzene is released from a benzene storage tank located outside but near a plant for producing benzene embodying an absorption system, the process of the present invention may be integrated with such benzene production facility. Thus, in accordance with such an integrated scheme, the extraction solvent employed in line 17 is identical to the extraction solvent employed in the benzene production plant. Thus, the lean extraction solvent in accordance with such an embodiment is in fact the lean extraction solvent regenerated in benzene plant 18.

The amount of lean extraction solvent employed in line 17 is substantially less than the volume rate of absorption oil employed in line 13, and in general, is proportionate to the amount of benzene in the rich absorption oil in line 15. In general, the molar ratio of extraction solvent to benzene present in the oil in line 15 is in the order of from 5 to 1 to 10 to 1, most generally in the order of from 6 to 1 to 7 to 1. This molar ratio is in general one third ($\frac{1}{3}$) or less of the molar ratio of absorption oil to benzene used in the absorption step.

The exact amount employed is of course dependent upon the rate of gas flow and the temperature and pressure at benzene loading conditions. In accordance with the present invention, it is possible to effect 99% and better benzene recovery from a rich absorption oil.

The mixture of extraction solvent and absorption oil withdrawn from mixer 16 is introduced into a settler, schematically generally indicated as 19 in order to effect phase separation between the extraction solvent and absorption oil. As a result of the solvency power of the extraction solvent, the benzene is effectively extracted from the absorption oil into the extraction solvent phase.

Lean absorption oil is withdrawn from separator 19 through line 21, cooled in cooler 22 and introduced into the absorption tower 11 through line 13.

Benzene rich extraction solvent is withdrawn from separator 19 through line 23, and in accordance with one embodiment of the invention, such benzene rich extraction solvent in line 23 is returned to the benzene plant 18 wherein benzene can be economically recovered from the extraction solvent along with the benzene produced in the plant.

In accordance with another embodiment wherein it is not possible or desirable to integrate the recovery scheme of the present invention with a benzene production plant, the benzene rich extraction solvent withdrawn from separator 19 is passed through line 24, is heated in heat exchanger 32 and introduced into a stripping tower, schematically generally indicated as 25, which is provided with suitable equipment for providing reflux, schematically indicated as 26, and reboil, schematically indicated as 27. The stripper 25 is operated in order to effectively strip benzene from the rich extraction solvent to thereby recover benzene as product in line 28 and provide a lean extraction solvent for the extraction step. In general, the stripping tower 25 is operated at a bottoms temperature in the order of from 290° F. to 350° F., preferably in the order of from 300° F. to 320° F., and at a pressure in the order of from 6 to 15 psig, and preferably from 8 to 10 psig. The stripping tower 25 for effecting recovery of benzene from the extraction solvent requires heating and cooling duties which are considerably less than corresponding duties for recovering benzene from a rich absorption oil in view of the relative smaller amount of extraction solvent compared with absorption oil; in particular, such heating and cooling duties would be approximately one sixth of the corresponding duties for generating rich absorption oil.

Net benzene product is recovered from the tower 25 through line 28. Net lean extraction solvent recovered from tower 25, is heat exchanged in exchanger 32, further cooled in cooler 31 and passed to mixer 16 through line 17.

Although the invention has been particularly described with respect to recovering benzene vapor from a gas released from a benzene storage facility, the present invention is also applicable to recovery of other vaporized volatile liquids present in a gas released from a storage facility therefor; e.g., dienes (isoprene, butadiene, cyclopentadiene); acetylenics, olefins and other aromatics (toluene, xylene, etc.) and the like.

The present invention will be further described with respect to the following example; however, the invention is not to be limited thereby:

EXAMPLE

In a benzene tank loading facility for loading benzene into tank cars at a rate of 1200 gallons per minute, the cars are blanketed with nitrogen and are at a temperature of 100° F. Benzene concentration in the vent gas at a back pressure of 10 psig is 13 mol %.

Absorption tower 11 is operated at a gas inlet temperature of 100° F. and a pressure of 10 psig. The temperature rise of the oil through the tower is 6° F. The absorption tower has a diameter of 16 inches, a packed section height of 8 feet, a packing volume of 11 cu. feet, and employs 1 inch metal pall rings.

The extraction solvent employed in line 17 is tetraethylene glycol. The static mixer 16 is designed for complete mixing in 5 spiral stages with a pressure drop of approximately 5 psi. The settler 19 is sized for liquid phase separation requiring a retention time of about 15 to 20 minutes for the light phase liquid. Drum size is about 4 feet diameter by 12 feet tangent to tangent length. The cooler duty to remove the latent heat of benzene vapor is approximately 50,000 BTU per hour requiring about 5 gallons per minute of cooling water with a 20° F. rise.

The material balance is reported in the following table:

| | FEED | Mol/hr LEAN OIL | Mol/hr RICH OIL | VENT | LEAN* SOLV. | RICH SOLV. |
|---|---|---|---|---|---|---|
| $N_2$ | 23.5 | trace | trace | 23.5 | — | — |
| Benzene | 3.5 | trace | 3.5 | 1 ppm | trace | 3.5 |
| $O_2$ | trace | — | — | trace | — | — |
| Oil | — | 60 | 60 | — | — | trace |
| solv. | — | trace | trace | — | 19.8 | 19.8 |
| TOTAL | 27.0 | 60 | 63.5 | 23.5 | 19.8 | 23.3 |
| lbs/hr | 931 | 17400 | 17673 | 658 | 3850 | 4123 |
| GPM | — | 42 | 43 | — | 7 | 7.7 |
| CFM | 114 | — | — | 99.3 | — | — |

*Solvent based on Tetra Ethylene Glycol

The present invention is particularly advantageous in that it can be easily integrated with the volatile liquid producing plant for the effective recovery of a vapor, such as benzene, from a blanket gas. Furthermore, this scheme is simpler than compression, chilling and condensing. In addition, such absorption/extraction scheme, as presented is effected with a savings in regeneration heating and cooling duty. In addition, oxygen contamination of the solvent is eliminated as a result of the indirect method of benzene recovery.

These and other advantages should be apparent to those skilled in the art from the teachings herein.

Numerous modifications and variations of the present invention are possible in light of the above teachings and, therefore, within the scope of the appended claims, the invention may be practiced otherwise than as particularly described.

I claim:

1. A process for the recovery of a volatile liquid present as a vapor in a blanket gas released from a storage zone for the volatile liquid, comprising:
    (a) contacting said blanket gas containing the volatile liquid as a vapor with a lean absorption oil for said vapor, said absorption oil absorbing said vapor from said gas to provide a rich absorption oil containing an absorbed component consisting essentially of the volatile liquid and providing a remaining gas essentially free of the volatile liquid;
    (b) contacting rich absorption oil with an extraction solvent for said volatile liquid, said extraction solvent being immiscible with the absorption oil, said extraction solvent being employed in a molar ratio to volatile liquid which is one-third or less of the molar ratio of absorption oil to volatile liquid in step (a) and extracting said volatile liquid from the rich absorption oil to provide a lean absorption oil and a rich extraction solvent;
    (c) separating lean absorption oil from rich extraction solvent;
    (d) passing separated lean absorption oil without stripping thereof to said contacting with said blanket gas in step (a);
    (e) recovering said volatile liquid from the rich extraction solvent to provide a lean extraction solvent; and
    (f) passing lean extraction solvent to said contacting with the rich absorption oil in step (b).

2. The process of claim 1 wherein the contacting of step (b) is conducted in an in-line static mixer.

3. The process of claim 1 wherein the volatile liquid is recovered from the rich extraction solvent by stripping.

4. The process of claim 1 wherein the volatile liquid is benzene.

5. The process of claim 4 wherein the absorption oil is of an aliphatic character.

6. The process of claim 5 wherein the absorption oil has a boiling point of at least 400° F.

7. The process of claim 5 wherein molar ratio of extraction solvent to benzene in step (b) is from 5:1 to 10:1.

8. The process of claim 4 wherein the contacting of step (b) is conducted in an in-line static mixer.

9. The process of claim 8 wherein the volatile liquid is recovered from the rich extraction solvent by stripping.

10. The process of claim 9 wherein the absorption of step (a) is at a temperature of from 100° F. to 130° F. and a pressure of from 2 to 10 psig.

11. The process of claim 10 wherein benzene is stripped from extraction solvent at a bottoms temperature of from 290° F. to 350° F. and a pressure of from 6 to 15 psig.

12. The process of claim 4 wherein the recovery of benzene is integrated with a benzene production plant and the lean extraction solvent is derived from the benzene production plant.

13. The process of claim 4 wherein the extraction solvent is an ethylene glycol.

14. The process of claim 4 wherein the blanket gas consists essentially of nitrogen and benzene.

15. The process of claim 1 wherein the volatile liquid is a volatile aromatic liquid.

* * * * *